United States Patent [19]

Truppe

[11] Patent Number: 5,704,897
[45] Date of Patent: Jan. 6, 1998

[54] APPARATUS AND METHOD FOR REGISTRATION OF POINTS OF A DATA FIELD WITH RESPECTIVE POINTS OF AN OPTICAL IMAGE

[76] Inventor: Michael J. Truppe, Am Kanal 27, A-1110, Wien, Austria

[21] Appl. No.: 379,616
[22] PCT Filed: Aug. 2, 1993
[86] PCT No.: PCT/AT93/00126
     § 371 Date: Jan. 31, 1995
     § 102(e) Date: Jan. 31, 1995
[87] PCT Pub. No.: WO94/03100
     PCT Pub. Date: Feb. 17, 1994

[30] Foreign Application Priority Data

Jul. 31, 1992 [AT] Austria .................. 1557/92

[51] Int. Cl.$^6$ .................................. A61B 1/04
[52] U.S. Cl. .................... 600/117; 128/653.1; 128/922
[58] Field of Search ..................... 600/117, 103, 600/109, 921; 364/413, 13, 413.22, 413.19; 382/10, 6; 128/653.1

[56] References Cited

U.S. PATENT DOCUMENTS

| | | | |
|---|---|---|---|
| 4,722,056 | 1/1988 | Roberts et al. | 128/653.1 |
| 4,922,909 | 5/1990 | Little et al. | 364/413.13 |
| 5,099,846 | 3/1992 | Hardy | 128/653.1 |
| 5,261,404 | 11/1993 | Mick et al. | 128/653.1 |
| 5,291,889 | 3/1994 | Kenet et al. | 128/653.1 |
| 5,336,880 | 8/1994 | Leclerc et al. | 378/207 |
| 5,409,001 | 4/1995 | Seyler et al. | 128/653.1 |
| 5,417,210 | 5/1995 | Funda et al. | 128/653.1 |

*Primary Examiner*—Lynne A. Reichard
*Assistant Examiner*—John P. Leubecker
*Attorney, Agent, or Firm*—Broadbent, Hulse Pierce & Pate

[57] ABSTRACT

An apparatus and method enables a precise superimposition of an optical representation with a data field to support the navigation during endoscopic operations. An optical representation is acquired by an endoscope with a camera and displayed on a screen. A sensor is attached to the endoscope or camera to continuously detect its spacial position. A spacial data field is also acquired, from such techniques as X-ray tomography, NMR tomography or ultrasound, and allocated to a body in a certain position. A sensor which is adapted to be attached to the body compensates for any movement of the body. A computer is provided for registering selected points of the data field with respective points of the optical representation by displacement certain points of the data field while superimposed on the optical representation.

9 Claims, 7 Drawing Sheets

APPARATUS AND METHOD FOR REGISTRATION OF POINTS OF A DATA FIELD WITH RESPECTIVE POINTS OF AN OPTICAL IMAGE

BACKGROUND

1. Field of the Invention

The invention relates to a method for representing the interior of bodies with the following steps:

Providing an optical imaging system consisting of a camera and a monitor;

allocation of a spatial data field to the body disposed in a certain position;

continuous detection of the spatial position of the camera;

continued calculation of a representation of the data field which corresponds to the current angle of view of the camera;

simultaneous or alternative representation of the optical image and the data field on the monitor.

2. The Background Art

Endoscopes are used with increasing frequency in operations so as to reduce the stress for the patients. During this process the endoscopic image is represented on a video monitor. This means a substantial change in operating technique for the doctor.

In common operations the operating field is freely accessible to the eye, and there is a natural coordination of the hand movements. This is no longer the case in operations by means of an endoscope. There is no connection between the orientation of the endoscope and the direction of view of the user, i.e., the operating surgeon. As a result of this the movement of surgical instruments relative to the endoscope becomes dependent on the surgeon's faculty of three-dimensional visualization. The second disadvantage is the lack of spatial feeling, as usually only one endoscopic lens is used. For each operation it is generally necessary to have knowledge of organ and tumor borders and the anatomical situation. An overview over the operating field facilitates orientation.

The third aspect is planning the operation. In a freely accessible operating field there is a clear sequence of operating steps. The surgical instruments can be used intuitively. The operation by means of endoscopes places higher requirements. Even the positioning of the surgical instruments relative to the operating field requires planning.

In the field of stereotactic surgery there are methods which can be used in principle for endoscopical surgery too.

From DE-A 37 17 871 it is known to mix in data such as computer tomography (CT) representations into the operating microscope in order to obtain help in the navigation of surgical instruments. The represented CT-layers correspond to the plane to which the microscope is focussed. During a movement of the instrument the respective layers are displayed dynamically on the computer screen. The surgeon is to be supported in this way in the positioning of an instrument relative to an anatomical structure. In order to bring the microscopic image with the CT-representation into alignment, it is necessary that certain points which are marked by means of a laser beam are aimed at with the microscope and that thereafter the microscope is focused therethrough.

U.S. Pat. No. 4,722,056 describes a method in which a tomography image is overlapped with the focal plane of an operating microscope. The representation of a CT-layer is adjusted to the optical representation.

DE-A 41 34 481 relates to a microscope for stereotactic microsurgery. A laser locating system is used for determining the position of the microscope relative to the patient. The function is similar to that of the microscope which is described in U.S. Pat. No. 4,722,056.

In EP-A 488 987 of the applicant a method is described for overlapping data and optical representations. With this method it is possible, for example, to mix in axes of extremities into an optical representation in realtime.

In the field of endoscopic surgery complete CT-series of findings are rarely available. Moreover, the spatial reproduceability of the position of anatomical structures is limited primarily to the skull. In the abdominal region the intraoperative condition is not deduceable from a preoperative CT without any special measures. Furthermore, computer tomography is a relatively complex method which is not always readily available or cannot be used.

These known methods assume that the position of the patient prior to the operation can be determined definitely relative to a spatial coordinate system with all three axes of freedom. This can be made, for example, by focussing marking points with an operating microscope. After the determination it is necessary that the patient remain rigidly fixed, i.e., the patient must be strapped in a fixed manner to the operating table. The position of the microscope is detected in this known method via the rod structure or via position sensors, so that a CT-representation or the like can be brought in relationship to the image plane, which allows a superimposition of this representation with the optical image.

These methods are used primarily in the field of stereotactic surgery. A surgical instrument is to be guided towards a tumor, for example. The position of the tumor is reconstructed from CT-findings. No change in the position of the patient per se or the position of the operating field within the patient may occur after acquiring the position of the patient, i.e., particularly during the operation.

However, a completely rigid fixation of a patient is not always possible. Moreover, additional difficulties occur particularly during endoscopic operations. The endoscope is moved to the target zone through open cavities in the body. These are generally relatively flexible and therefore rarely correlate with CT-findings. Moreover, tissue may frequently be displaced considerably during an operation, e.g. by removing parts of tissue, suction of liquid, etc. As a result of this the representation of the data field correlates less and less with the optical image and the information provided becomes increasingly worthless.

Moreover, it is to be observed that owing to the limited precision of position sensors an optimal determination of position is always only possible for a specific spatial volume. Marking points which under certain circumstances may be relatively far away from the target zone as is generally the case in endoscopic methods are not optimal with respect to the achievable precision. Finally, a certain temporal drift occurs in position sensors so that unavoidable deviations will occur during longer operations.

BRIEF SUMMARY AND OBJECTS OF THE INVENTION

It is the object of the present invention to avoid said disadvantages and to provide a method which enables a precise superimposition of the optical representation with a data field, e.g., a CT-representation, during the use of an endoscope too.

It is a further object of the invention to provide a method for supporting the navigation during endoscopic operations which can be used without the presence of representations from computer tomography.

This object is achieved in that an endoscope is series-connected to the camera, that a calibration is carried out repeatedly which consists of bringing in conformity one or several characteristic points of the data field with the pertinent optical representation on the screen by an entry process of the user.

The substantial element in the invention is that marking points, as in the state of the art, are only used for "rough navigation", if required. This allows approximate aiming at the target region. In the actual navigation the user is free in the choice of the points used for re-calibration. The re-calibration can therefore always be made in the region of particular interest, thus maximizing the precision in this region. In contrast to the methods of the state of the art, in which the work practically proceeds from the outside to the inside, the process of the present invention can be designated as a process from the inside to the outside.

When using novel 3D-sensors sensing chips, which have a size of approx. 1 mm$^2$ only, it is possible to secure a plurality of such sensors to the patient in order to create a local reference coordinate system. Approx. 100 of such sensors can be applied in the liver region. The re-calibration in accordance with the invention is bringing an optical image into registration with the determination of the position by reference sensors.

A representation gained from an imaging method such as X-ray tomography, NMR tomography, an ultrasonic representation or the like can be used as a data field. In order to obtain representations which are more descriptive than common sectional representations it is possible to rework the CT-findings in order to maintain characteristic points or lines which are particularly suitable for comparisons or for renewed finding. Such a method may be as has been described, for example, by N. Ayache et al.: "Evaluating 3D Registration of CT-Scan Images Using Crest Lines", in: SPIE Vol. 2035 Mathematical in Medical Imaging II (1993), p. 60.

It is particularly advantageous when a three-dimensional reconstruction is used as a data field which is obtained from previously made video recordings. In this way it is possible to provide a navigational aid within the scope of the invention without allowing the necessity to arise that a CT-representation has to be made. Either prior to the operation or in an early stage of the operation a local 3D-reconstruction of the operating field is made. This allows a precise planning of the operation. After carrying out changes in the operating field, e.g., by excision of parts of tissue, tumors, etc., the representation of the condition existing beforehand can be overlapped with the current condition.

It is possible that the three-dimensional reconstruction is obtained from a single video recording to which a distance measurement is allocated, e.g., via ultrasonic sound.

On the other hand, the three-dimensional reconstruction can be obtained from several video recordings by stereometric analysis. Such a stereometric analysis is known, for example, from P. Haigron, : "3D Surface Reconstruction Using Strongly Distorted Stereo Images", in: IEEE, Proceedings of the Annual Conference on Engineering in Medicine and Biology (1991), IEEE cat. n. 91CH3068-4, p. 1050f. This paper describes the reconstruction of the surface of the femur in the knee area by distorted endoscopic images. The spatial reconstruction from single images is described in a general way by Fua. P.: "Combining Stereo, Shading and Geometric Constraints for Surface Reconstruction from Multiple Views", in SPIE Vol. 2031 Geometric Methods in Computer Vision II (1993), p. 112ff.

It is advantageous if the displacement of the points is made by means of a computer mouse. It is not always possible to target specific points which are to be used for recalibration with the endoscope which is inserted into a body cavity so that they come to lie precisely in the graticule. It is far easier to bring the points of interest only into the field of vision of the endoscope and then to fix the image, i.e., to freeze it, and then to carry out the matching. In this process it is also possible to process several points simultaneously.

It may further be provided that the endoscope is used for examining a patient to which a position sensor is attached so as to compensate any changes in the position of the patient. This measure allows moving the patient also during the work with the endoscope. When the coordinate system of the target zone is not displaced relative to the coordinate system of the whole patient, a re-calibration is not necessary.

The invention further relates to an apparatus for carrying out the above method. The apparatus may include the following elements:

a camera with an endoscope attached thereto;

a position sensor attached to the camera or the endoscope;

a monitor for displaying the optical image recorded by the camera together with a data field;

a computer with a memory for the data field and means for detecting the position of the position sensor.

The apparatus is characterized in that means are provided which allow the user to bring into conformity points of the data field with respective points of the optical image and thus to improve the conformity between the other representation of the data field with the optical image. These means may include, for example, a mouse as is used frequently as an input medium for computers and of respective algorithms for the readjustment of the coordinate transformations so as to obtain from the entry of the user a better "fit" between the optical representation and the representation of the data field.

The invention is now explained in closer detail by reference to an embodiment shown in the drawings, in which.

BRIEF DESCRIPTION OF THE DRAWINGS

DETAILED DESCRIPTION OF THE PREFERRED EMBODIMENTS

Figure 1:
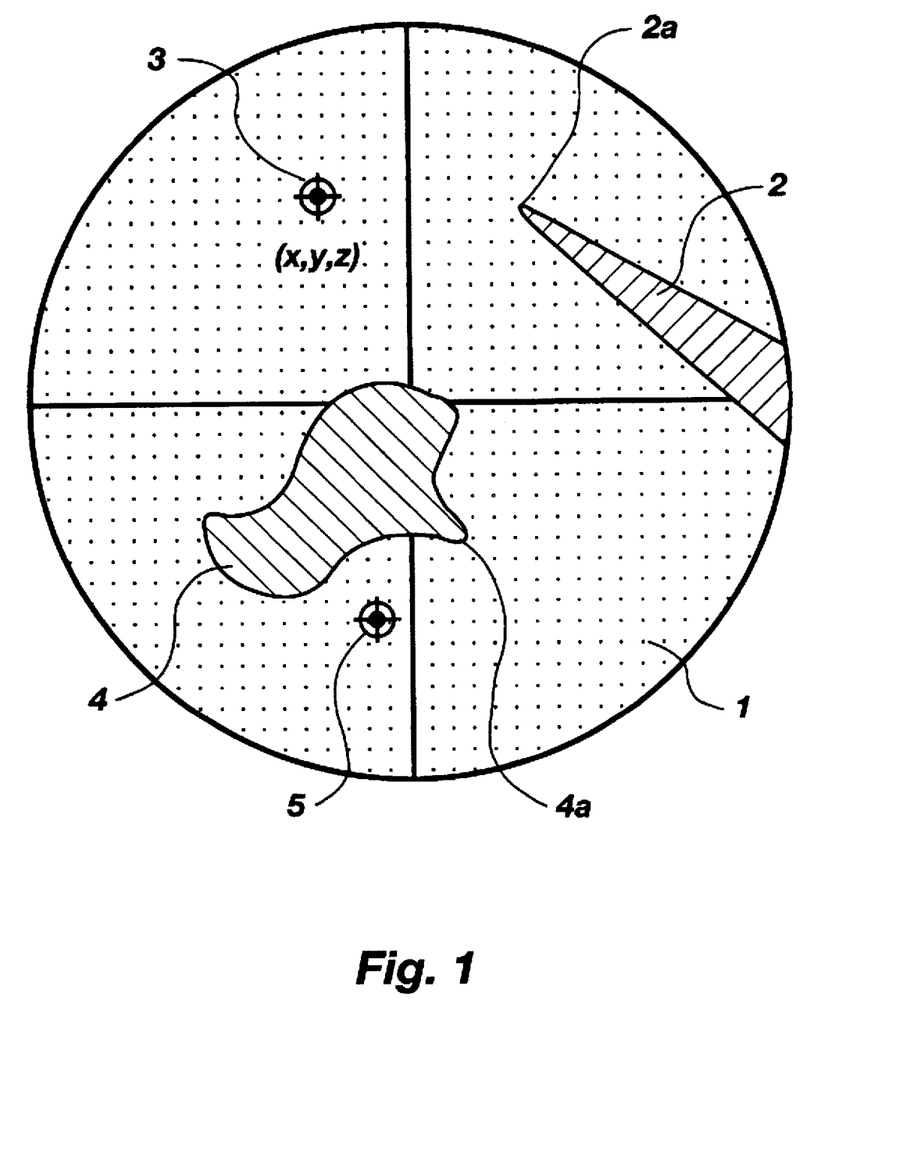
FIG. 1 shows schematically the representation of an endoscopic image on the monitor prior to calibration.
Figure 2:
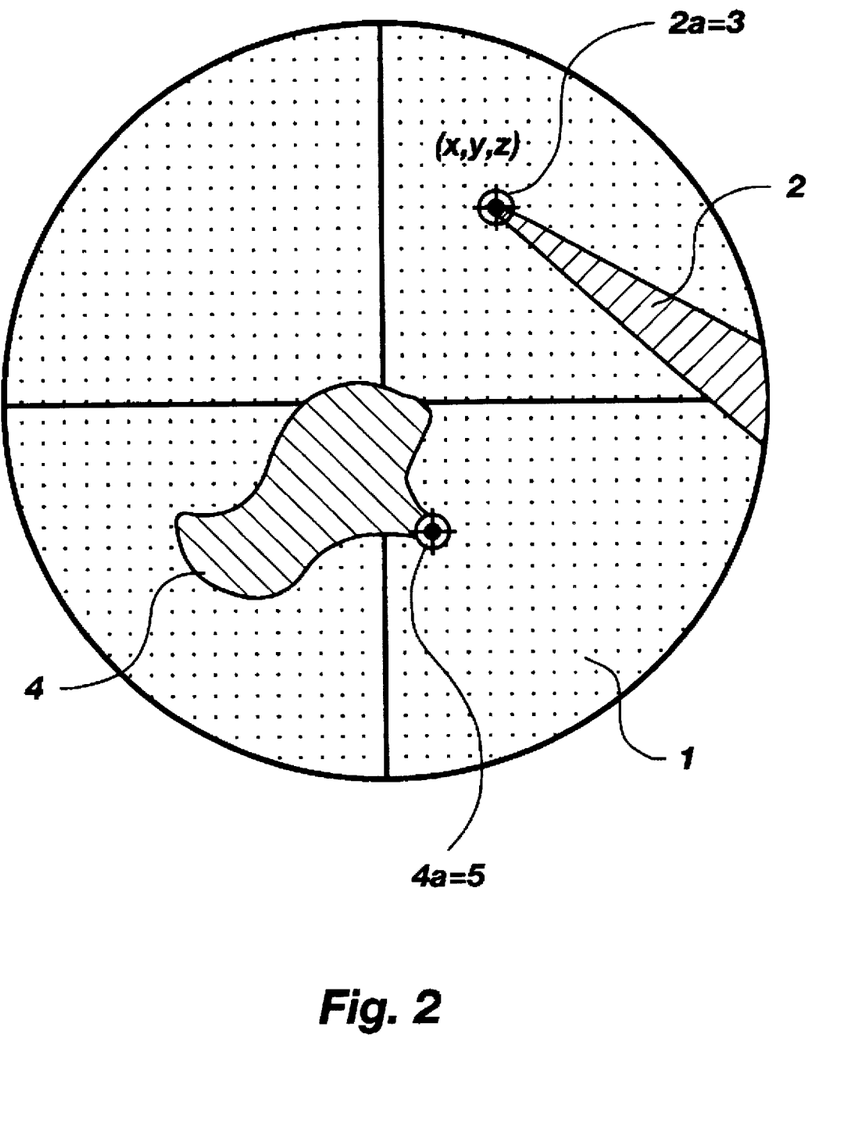
FIG. 2 shows a respective representation after the calibration.

Image section 1 shows an instrument 2 with a tip 2a. The point 3 represents the cross-faded calculated position of the tip, i.e., the "virtual" image of the tip. In FIG. 1 the real image 2a and the virtual image 3 fall apart. By making respective adjustments it is possible to bring the images into conformity, as is shown in FIG. 2. The calibration is thus completed.

In the same way it is possible to carry out the calibration with a characteristic point 4a of a represented object 4. In FIG. 1 the optical representation 4a and the virtual image 5 fall apart. After the calibration this is no longer the case.

Figure 3:
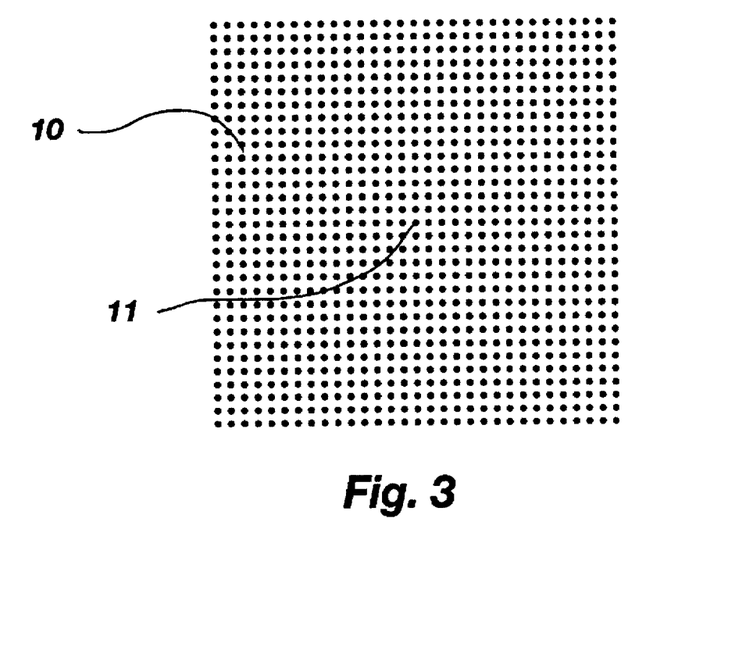
FIG. 3 shows a test image for correcting the distortion of the endoscopic image.
Figure 4:
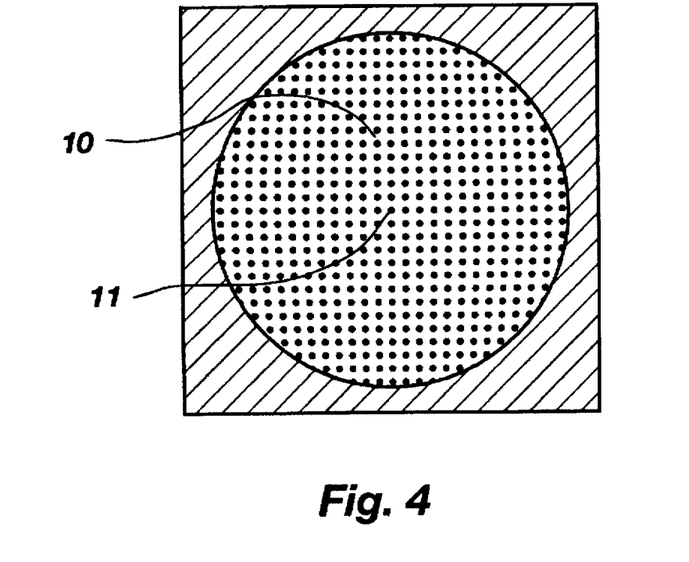
FIG. 4 shows the representation of the test image which is distorted by the endoscope.

The test image shown in FIG. 3 includes points 10 arranged evenly in a square pattern. The points 10 may be represented by dots of suitable size or may be connected by lines. This image is distorted by the optical system of the endoscope, as is shown in FIG. 4. A respective overlap of other representations is thus provided with errors, which are the greater the farther the respective detail is disposed outside of the center 11. To improve the conformity the distorted position of the individual measured points 10 is determined by a respective image processing program. As the true position is known with the exception of a scaling factor determinable by the user, a distortion function can be calculated for the entire image plane. With mathematical methods which are known to the man skilled in the art it is possible to calculate a correction function by inverting this function, which removes the distortion. It is clear that this process must be carried out for each endoscope, as endoscopes of the same type can well be provided with different distortions. A pattern recognition method may be used to evaluate and correct distortions.

Figure 5:
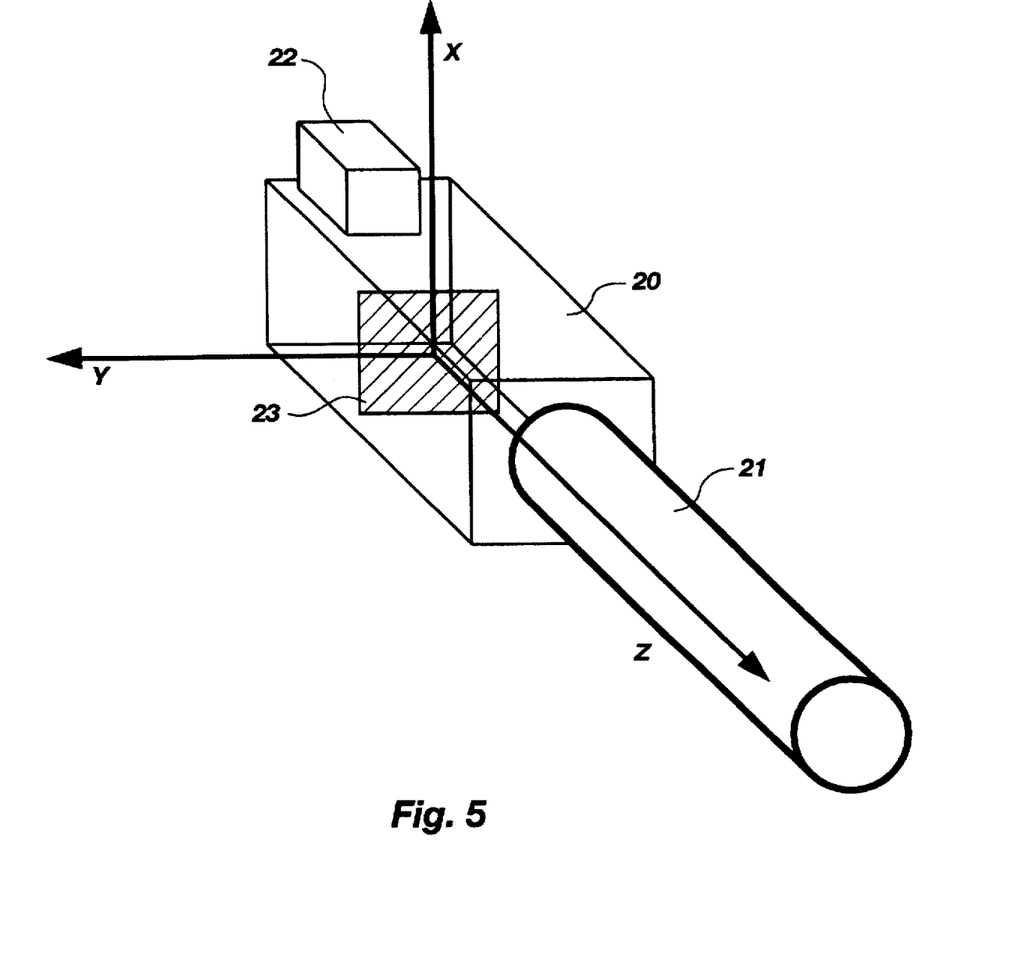
FIG. 5 shows schematically the endoscope attached to a video camera.

FIG. 5 shows a video camera 20 with an endoscope 21 attached thereto. The respective position of the camera 20, and thus of endoscope 21, is determined via a 3D-sensor 22. The image plane of the camera is designated with 23.

Figure 6:
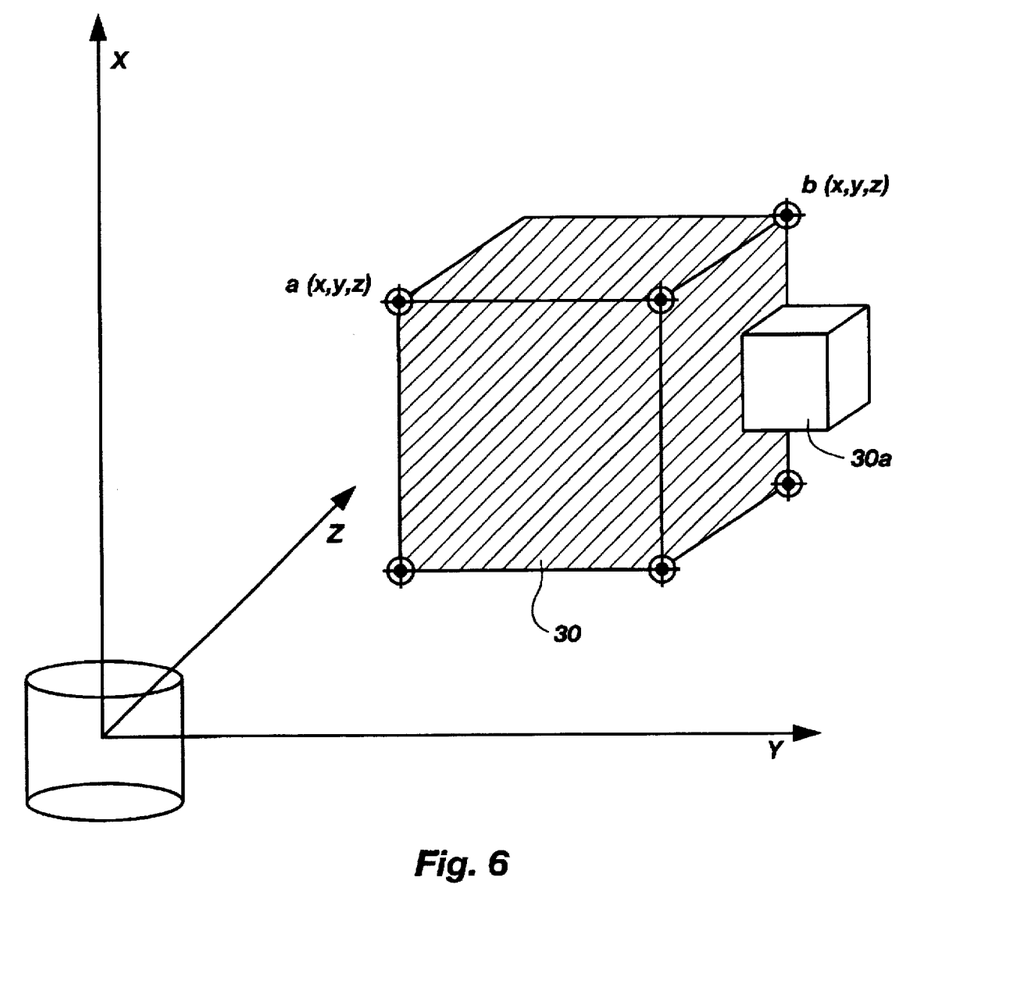
FIG. 6 shows schematically a reference object for determining the spatial position of the image plane.

FIG. 6 shows schematically a fixed reference object 30 in the form of a cube for determining the position of the image plane of the camera. The coordinates x, y, z of the corner points a, b of the cube in a spatial coordinate system are known. Either the coordinates of a cube 30 which is immobile in space is acquired with a 3D-digitizer or, as is shown in FIG. 6, a position sensor 30a is attached to cube 30, by means of which said cube 30 can be freely movable in space also during the determination of the position. In a symbolic drawing of this cube 30 which is shown on the screen the user must bring the corner points to a matching position with the frozen image by displacement. From this information the computer is enabled to calculate the coordinates of the image plane present at the time of freezing the image with the help of a direct linear transformation. With the help of the 3D-sensor 22 attached to camera 20 it is also possible to calculate the position of the image plane which might have possibly changed in the meantime.

Figure 7:
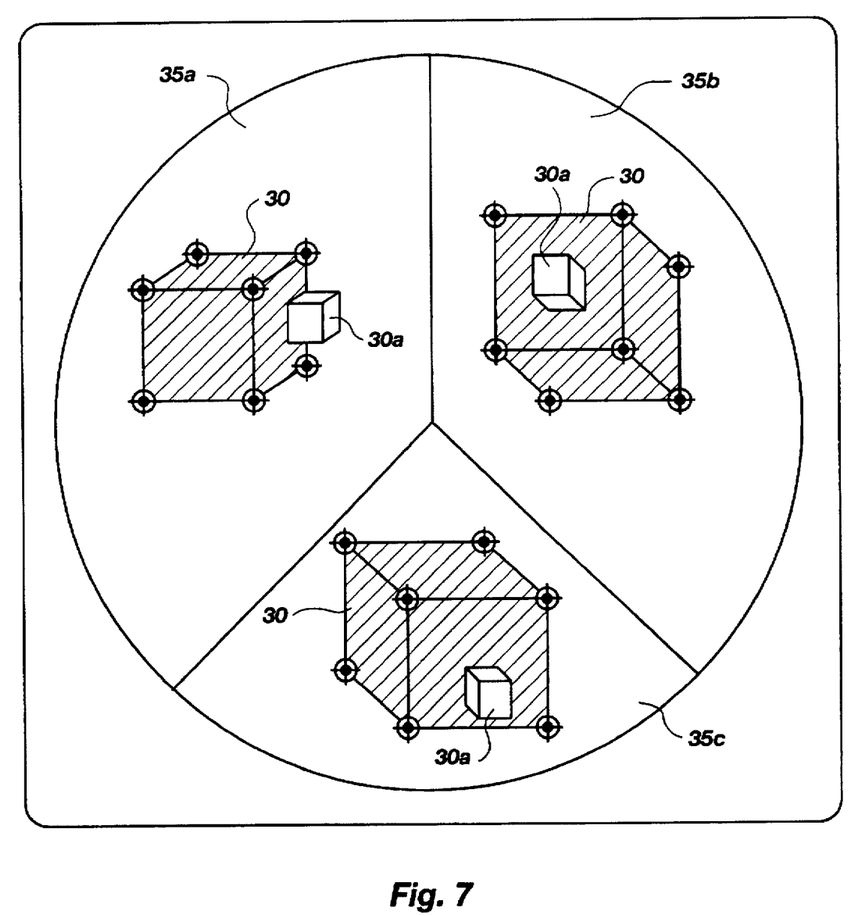
FIG. 7 shows a screen representation for calibrating the image plane of the camera.

FIG. 7 shows an image section which can be used in calibrating the position of the image plane. Representations of the reference object, namely cube 30, recorded from different positions are shown in three sectors 35a, 35b and 35c. In this way it is possible to carry out a plurality of calibrating measurements in a single image representation in order to maximize the precision.

As an alternative to an actually existing reference object it is also possible to use a "virtual reference object" for calibrating the endoscope. A camera 20 is aimed at the tip of a 3D-stylus. A 3D-stylus is a device of the size of a ballpoint pen which can issue data on the spatial position of its tip at any time via built-in magnetic coils. The calibration of the endoscope is made in such a way that the camera is aimed at the 3D-stylus. The image is then fixed, i.e., it is frozen, and a cursor disposed on the screen is moved with a mouse or joystick to the representation of the tip. This process is carried out at least six times. In this way a precise calibration of the endoscope is possible.

The precision of the overlapping can be made in a very simple and clear manner in that the 3D-stylus is brought into the image. The optical representation of the tip and the symbolic display gained from the coordinates have to be precisely above one another in the case of an optimal adjustment. Any distance shows an imprecise adjustment of the coordinate systems.

Figure 8:
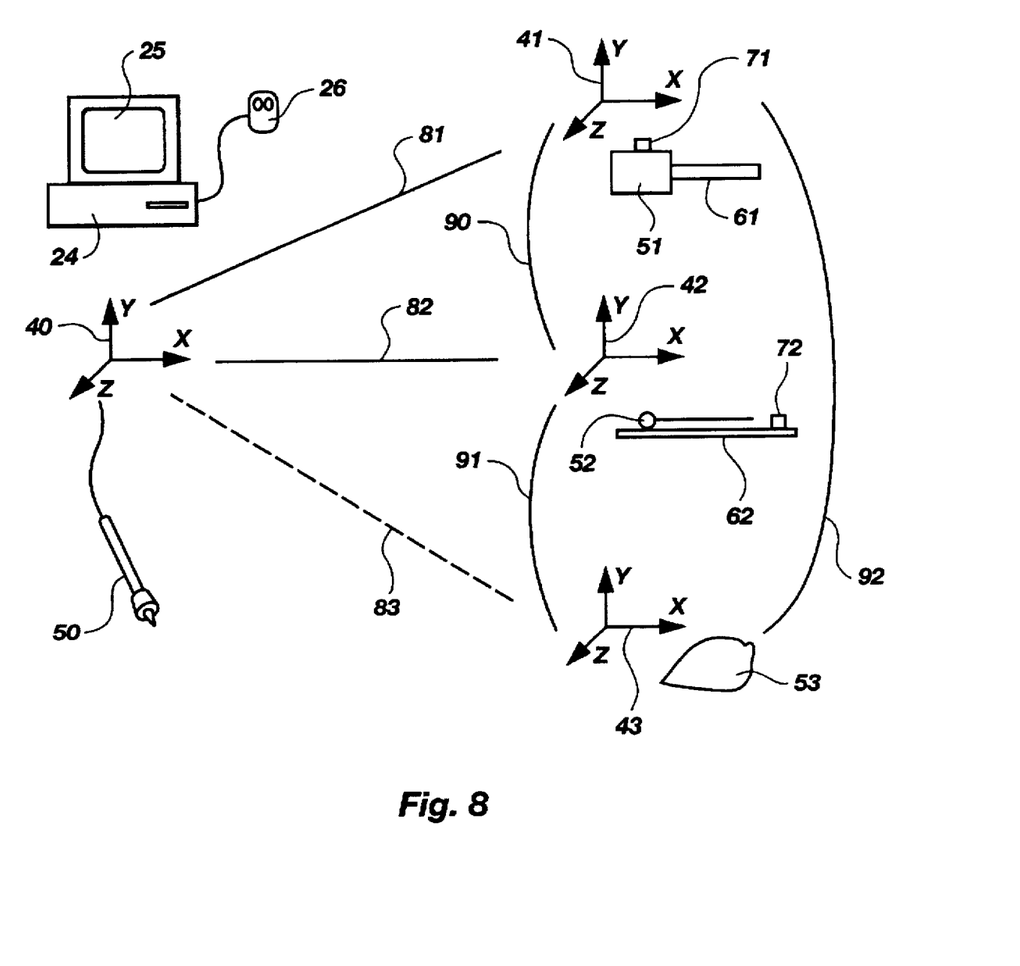
FIG. 8 shows schematically the different coordinate systems and their relationships, including the hardware involved.

FIG. 8 schematically shows the spatial coordinate system 40. It is represented by way of example by the digitizer stylus 50, with which the coordinates of every spatial point can be determined by scanning. The coordinate system 41 is the one of endoscope 61 or the camera 51 fixedly attached thereto. The current position is detected via the fixedly attached position sensor 71. The calibration of the image plane is made once via a reference object or a virtual reference object, as is described above. In this way the relationship 81 between coordinate systems 40 and 41 is determined for the duration of the endoscopic examination.

A position sensor 72 may be attached to patient 52, who may lie on an operating table 62. The relationship 82 to the spatial coordinate system is determined by a one-off adjustment, and thus relationship 90 is determined too.

The target zone is indicated with reference numeral 53. Its coordinate system, which is also the one of the data structure, can be detected roughly at first by a setup on the basis of external conditions. A direct tracing is not possible, which is why the relationship 83 is shown in a broken line. The method in accordance with the invention, however, allows establishing the relationship 92 to the camera 51 or the endoscope 61, by means of which relationship 91 is also determined. When relationship 91 changes, e.g., after the removal of parts of tissue, it is necessary to perform a re-calibration in accordance with the method of the invention.

The required calculations are made in computer 24 and displayed on monitor 25. The mouse 26 is used for carrying out the recalibration.

The optical image and the date image may each be displayed separately. Alternatively, a user may selectively view the optical image and the data image as superimposed images displayed on the monitor.

I claim:

1. A method for representing the interior of bodies, the method comprising:

providing an optical imaging system comprising a camera and a monitor, wherein an endoscope is connected in series with the camera to create an optical image;

attaching a position sensor to a body to compensate for changes in position of the body;

allocating a spatial data field to the body disposed in a certain position;

identifying points on the body and identifying characteristic points, corresponding thereto, in the data field;

calibrating the optical imaging system by registering the characteristic points with the points on the body;

detecting continuously the spatial position of the camera;

calculating a representation of the data field corresponding to a current angle of view of the camera; and selectively representing the optical image, the data field, and both the optical image and the data field superimposed, on the monitor.

2. A method as claimed in claim 1, wherein the data field is provided by using an imaging method selected from X-Ray tomography, NMR tomography, and ultrasonic imaging.

3. A method as claimed in claim 1, further comprising obtaining a video recording of the image and providing a three-dimensional reconstruction thereof.

4. A method of claim 3, wherein the three-dimensional reconstruction is gained from a single video recording to which a distance measurement is allocated.

5. A method of claim 3, wherein the three-dimensional reconstruction is gained from several video recordings by stereometric analysis.

6. A method of claims 1 to 5, further comprising an entry process comprising freezing the optical image superimposed on the data field at a time determined by a user, and wherein individual points of the data field are displaceable on the monitor in said frozen optical image.

7. A method as claimed in claim 6, wherein the displacement of the points is made by means of a computer mouse.

8. A method of claim 1, comprising the step of correcting a distortion of the optical imaging system by aiming the endoscope towards a test image comprising regularly arranged symbols, evaluating the symbols using a pattern recognition method, and calculating a correction function for the optical system.

9. An apparatus for imaging the interior of bodies; the apparatus comprising:

a camera having an endoscope operably attached thereto;

a first position sensor attached to the camera or the endoscope to provide a frame of reference with respect to the camera;

a second position sensor adapted to be attached to a body to compensate for changes in position of the body;

a monitor for displaying an optical image recorded by the camera together with a data field representing a model to be superimposed on the optical image;

a computer comprising a memory device for storing the data field representing the model;

means for detecting the position of the first position sensor; and means for registering selected points of the data field representing points of the model with respective points of the optical image by displacement of a second image corresponding to at least one point of the data field displayed on the monitor to be superimposed on the optical image.

* * * * *